United States Patent [19]
Johnson

[11] Patent Number: 5,655,544
[45] Date of Patent: *Aug. 12, 1997

[54] ENDOSCOPIC ASSISTED ABDOMINOPLASTY

[76] Inventor: Gerald W. Johnson, 16000 Steubner Airline #105, (Spring) Houston, Tex. 77379

[*] Notice: The term of this patent shall not extend beyond the expiration date of Pat. No. 5,329,943.

[21] Appl. No.: 419,383

[22] Filed: Mar. 30, 1995

[51] Int. Cl.$^6$ ......................................................... B31B 1/00
[52] U.S. Cl. ........................ 128/878; 128/897; 606/139
[58] Field of Search ................................. 128/897, 898; 604/49, 51; 606/1, 119, 139, 142, 143, 144, 148, 219, 220, 2, 52, 32

[56] References Cited

U.S. PATENT DOCUMENTS

| | | | |
|---|---|---|---|
| 3,807,407 | 4/1974 | Schweizer | 606/145 |
| 4,754,745 | 7/1988 | Horowitz | 600/8 |
| 5,254,132 | 10/1993 | Barley et al. | 606/214 |
| 5,329,943 | 7/1994 | Johnson | 128/898 |

Primary Examiner—Lee S. Cohen
Assistant Examiner—Rosiland Kearney
Attorney, Agent, or Firm—Neal J. Mosely

[57] ABSTRACT

A surgical procedure is an endoscopic assisted abdominoplasty. This procedure eschews the use of abdominal incisions and obtains the desired result with no visible scars on the abdomen of the patient. A traditional or standard abdominoplasty (also called a dermolipectomy of the abdomen) has always required a surgical incision in the abdomen followed by surgical removal of part of the skin, the underlying fat layer, and suturing the opening. The endoscopic assisted abdominoplasty shown herein uses two small hidden incisions, one in the umbilicus or on the abdomen or other areas, in pre-existing scars or other areas such as under the armpit for introduction of the surgical instruments, and a small incision within the pubic hair line for endoscopic and/or direct observation and control of the procedure. While observing the procedure through the endoscope, the surgical instruments are inserted through the umbilical incision to remove fat by liposuction and plicate and repair the muscles by use of a tenaculum and fascial sutures. After removal of the instruments, the small incisions are sutured and the skin layer allowed to retract and tighten. The procedure has had considerable success and leaves no visible scars, which is of great importance to most patients.

17 Claims, 10 Drawing Sheets

BABCOCK

FLESCH-THEBESIUS WHEISHEIMER

GALTIER

KELLY

KÜSTER

PICK, BARSKY GONZALEZ-ULLOA

SCHEPELMANN

THOREK

WEINHOLD

ENDOSCOPIC ASSISTED ABDOMINOPLASTY

BACKGROUND OF THE INVENTION

Cross Reference to Related Application

This application is an additional embodiment to the invention disclosed in applicant's U.S. Pat. No. 5,239,943, filed Jul. 12, 1995 and issued Jul. 19, 1994.

Field of the Invention

This invention relates to new and useful surgical procedures and more particularly to an endoscopic assisted abdominoplasty which eschews the use of large abdominal incisions and leaves no visible scars on the patient.

Brief Description of the Prior Art

Abdominoplasty (sometimes called a dermolipectomy of the abdomen) is a procedure which has been known for more than one hundred years. The procedure has always required a surgical incision in the abdomen followed by surgical removal of part of the skin, plication of the fascia with suturing, and finally suturing of the incision in the skin.

"*Reconstructive Plastic Surgery*", Second Edition, Volume 7 "The Lower Extremity The Trunk The Genitourinary Tract, Chapter 92 "*Dermolipectomy of the Abdominal Wall, Thighs, Buttocks, and Upper Extremity*" by Ivo Pitanguy, M.D.; 1977 W. B. Saunders Company is a treatise on dermolipectomy of the abdomen. Several traditional or standard procedures are described and shown.

"*ABDOMINOPLASTY*" by Frederick M. Grazer, M.D. *Plastic and Reconstructive Surgery* 51 No. 6 June 1973 The Williams and Wilkins Company, Baltimore, Md. 21202, pp. 617–623, describes further procedures in abdomino plasty of the abdomen.

References are given in both publications to many additional reports on varied procedures for abdominoplasty or dermolipectomy of the abdomen.

Acknowledgement is made to both authors for the use of some of their material in describing traditional or standard procedures for abdominoplasty or dermolipectomy of the abdomen.

According to "*Reconstructive Plastic Surgery*", Second Edition, Volume 7, Chapter 92, p. 3800–3807, the first dermolipectomies of the abdominal wall were performed by surgeons who were repairing massive umbilical hernias. The dermolipectomy facilitated the herniorrhaphy and relieved the patient of a pendulous abdomen. A number of procedures are described which illustrate the development of this surgical procedure. The classic lipectomy incisions are shown in FIG. 92-2 on page 3802 of the text. These illustrations of the various incisions are reproduced herein as FIG. 1A–1I of the drawings illustrating the prior art. The author of the text (Ivo Pitanguy, M.D.) reports an improved procedure using a lower abdomen incision to reduce the visibility of the resulting scar. In "ABDOMINOPLASTY" by Frederick M. Grazer, M.D. *Plastic and Reconstructive Surgery* 51 No. 6 June 1973, the author reports (at pp. 617–623) a modified Pitanguy technique which confines the final scar to the "bikini" area. For a more detailed description, one should consult the full text of the reference.

Other pertinent references are:

Wilkinson, T. and Swartz, B. Individual Modifications in Body Contour Surgery: The "Limited Abdominoplasty. Plast. Reconstr. Surg. 77:779, 1986.

Converse, J. Reconstructive Plastic Surgery. In J. M. Converse and J. G. McCarthy (eds.). Dermolipectomy of the Abdominal Wall, Thighs, Buttocks and Upper Extremity, 2nd Ed. Philadelphia: Saunders Company, 1977. Pp 3800–3823.

Wilkinson, T. Letter to the Editor. Plast. Reconstr. Surg. 86:1039, 1990.

Barrett, B. M., Jr. Combined Abdominoplasty and Augmentation Mammaplasty through a Transverse Suprapubic Incision. Ann. Plast. Surg 4:286, 1980.

Hester, T., Jr. Abdominoplasty Combined with Other Major Surgical Procedures: Safe or Sorry? Plast. Reconstr. Surg. 83:997, 1989.

Ersek, R. and Schade, Kris Subcutaneous Pseudobursa Secondary to Suction and Surgery. Plast. Reconstr. Surg. 85:442, 1990.

Johnson U.S. Pat. No. 5,329,943 discloses an endoscopic assisted abdominoplasty. This procedure eschews the use of abdominal incisions and obtains the desired result with no visible scars on the abdomen of the patient. The endoscopic assisted abdominoplasty shown in the patent uses two small incisions, one in the umbilicus for introduction of the surgical instruments, and a small incision within the pubic hair line for endoscopic observation and control of the procedure. While observing the procedure through the endoscope, the surgical instruments are inserted through the umbilical incision to remove fat (by liposuction) and plicate and repair the muscles (by use of a tenaculum and fascial staples or a single instrument which combines the function of these instruments). After removal of the instruments, the small incisions are sutured and the skin layer allowed to retract and tighten. The procedure has had considerable success and leaves no visible scars, which is of great importance to most patients.

SUMMARY OF THE INVENTION

One of the objects of the invention is to provide a new and improved surgical procedure for abdominoplasty of the abdomen.

Another object of the invention is to provide a new and improved surgical procedure for abdominoplasty of the abdomen which is essentially free from visible scars.

Another object of the invention is to provide a new and improved surgical procedure for abdominoplasty of the abdomen which is easily performed and is essentially free from visible scars.

Another object of the invention is to provide a new and improved surgical procedure for abdominoplasty of the abdomen which relies on and allows the natural elasticity of the skin to cause the undermined skin to contract or shrink down to conform to the new abdominal wall, thereby not requiring the long incisions needed to remove skin and leaving long ugly scars.

Still another object of the invention is to provide a new and improved surgical procedure for abdominoplasty of the abdomen which combines several surgical techniques into a completely new procedure to avoid extensive scars on the abdomen.

Still another object of the invention is to provide a new and improved surgical procedure for abdominoplasty of the abdomen which utilizes small incisions hidden in the umbilicus or on the abdomen, inside the pubic hair line, in pre-existing scars or other areas such as under the armpit, Still another object of the invention is to provide a new and improved surgical procedure for abdominoplasty of the abdomen which utilizes a full and complete undermining of the abdominal skin and fat (as done in the most extensive traditional or standard abdominoplasty) made possible by use of the Endoscope.

Stiff another object of the invention is to provide a new and improved surgical procedure for abdominoplasty of the abdomen which includes a complete and effective plication or repair of the muscles and abdominal fascia, from the xyphoid process to the pubis, made possible by use of the Endoscope and conventional or more advanced Endoscopic surgical suturing.

Yet another object of the invention is to provide a new and improved surgical procedure for abdominoplasty of the abdomen which includes a full and complete liposuction of the abdomen which is contraindicated in the traditional or standard abdominoplasty.

Yet another object of the invention is to provide a new and improved surgical procedure for abdominoplasty of the abdomen which is conducted by endoscopic procedure using surgical instruments inserted through a small incision, usually in the umbilicus, and direct viewing through an instrument inserted through a small incision located below the pubic hair line.

Yet another object of the invention is to provide a new and improved surgical procedure for abdominoplasty of the abdomen which is conducted by endoscopic procedure using surgical instruments, e.g. liposuction, tenaculum, and surgical needles, inserted through a small, incision, usually in the umbilicus, and endoscopic viewing through an instrument inserted through a small incision located below the pubic hair line.

Other objects of the invention will become apparent from time to time throughout the specification and claims as hereinafter related.

These and other objects of the invention are accomplished by a novel surgical procedure which is an endoscopic assisted abdominoplasty which eschews the use of abdominal incisions and obtains the desired result with no additional visible scars on the abdomen of the patient. The endoscopic assisted abdominoplasty uses two small incisions, one usually placed in the umbilicus for introduction of the surgical instruments, and a small incision within the pubic hair line for endoscopic observation and control of the procedure and introduction of instruments. While observing the procedure through the endoscope, the surgical instruments are inserted to plicate and repair the muscles (by use of a tenaculum and surgical suturing). After removal of the instruments, the small incisions are sutured and the skin layer allowed to retract and tighten. The procedure leaves no additional visible scars, which is of great importance to most patients.

DEVELOPMENT OF THE ENDOSCOPIC ASSISTED SURGICAL PROCEDURE

Figure 1A:
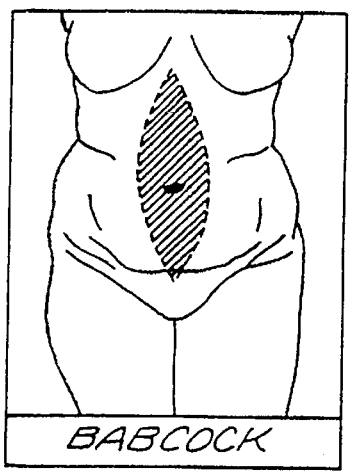
FIGS. 1A–1I are plan views illustrating a number of prior art incisions used by surgeons in performing an abdominoplasty of the abdomen according to traditional or standard procedures (taken from "Reconstructive Plastic Surgery", Second Edition, Volume 7, Chapter 92, p. 3802.
Figure 1B:
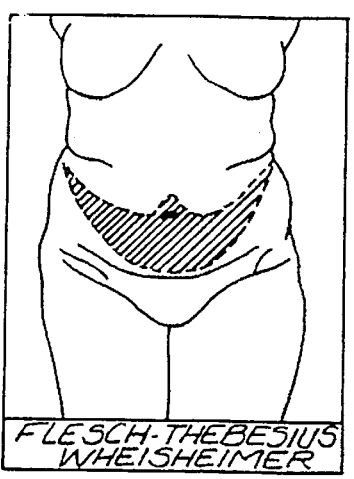
Figure 1C:
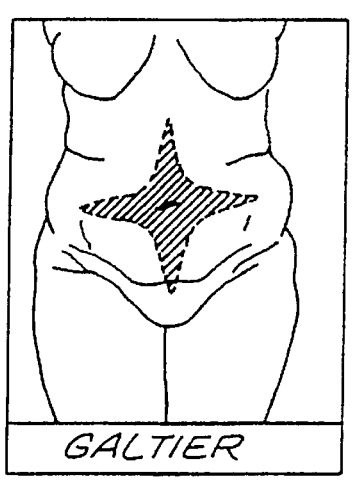
Figure 1D:
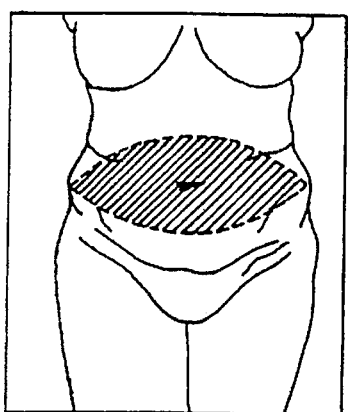
Figure 1E:
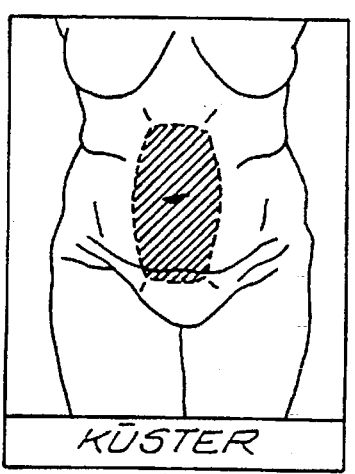
Figure 1F:
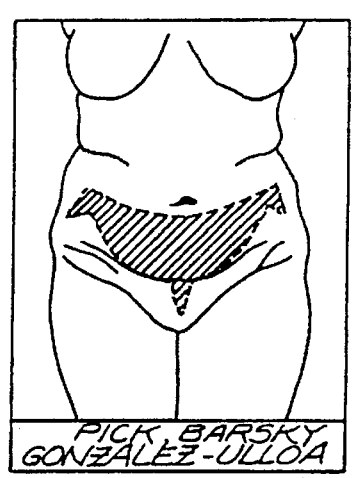
Figure 1G:
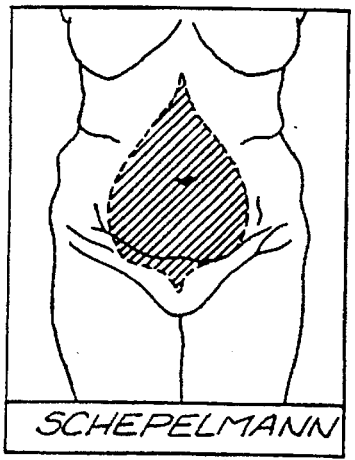
Figure 1H:
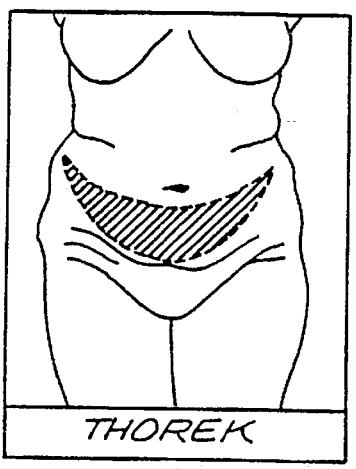
Figure 1I:
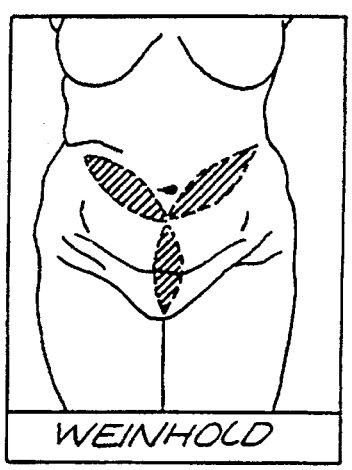
Figure 2:
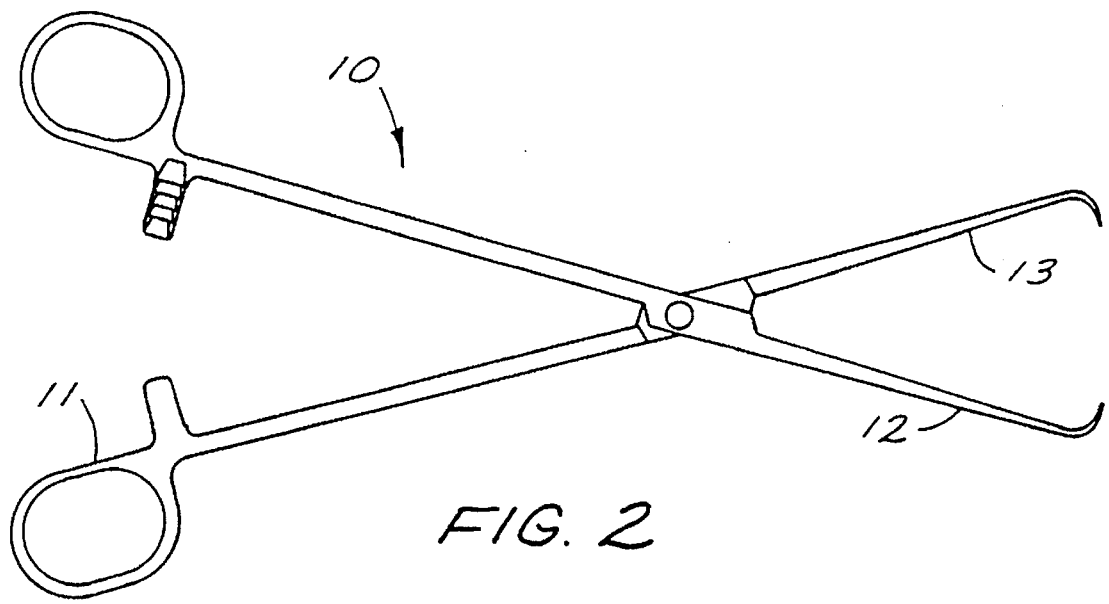
FIG. 2 is a plan view of a cervical tenaculum used in clamping the abdominal fascia during plication according to this invention.

At the start, ways were considered to complete the xiphoid to pubis repair of the lax anterior abdominal wall, fascia and muscle, through a limited incision. This type of procedure would be indicated to those patients who do not require excision of redundant skin, but often need an effective repair of the muscle and fascia, occasionally combined with liposuction of the anterior abdominal wall. A number of quality standards were set out to serve as goals for the procedure, as follows:

1. The acceptance of the procedure would depend on the ease with which the technique can be learned and successfully performed by the surgeon who can do the standard "open" abdominoplasty.

2. The quality of muscle, and fascia repair must be at least equal to that obtained using the "open" technique. In cases where no other scars are present on the abdomen, the endoscopic approach would be ideal.

From the inception of the concept of the no scar or limited incision abdominoplasty, it was apparent that the use of the endoscope would be required. Training with the endoscope was undertaken. Consideration was given to how to make a surgical approach through a 5 centimeter incision to allow dissection of the skin-subcutaneous pedicle cleanly away from the fascia. At the same time it would be necessary that hemostasis was secure as the dissection progressed.

The initial concept utilized a fiberoptic laser giving good dissection/hemostasis and usable to coagulate the smaller caliber blood vessels. Training was undertaken in the use of the fiberoptic laser, as well as the use of the laser and the endoscope together.

Then, a patient appeared requesting an abdominoplasty. She fit the requirements for the endoscopic abdominoplasty and she also had a longer than normal suprapubic scar from a prior hysterectomy. The scar could be used to convert to an "open" technique and gain more exposure if there were technical difficulties with the endoscopic technique.

Then, using a 60 watt YAG laser and a 10 mm 0 degree endoscope, with a 5 cm incision in the central portion of the existing suprapubic scar, the first attempted endoscopic abdominoplasty began. It quickly became apparent that dissection with the laser was not as effective as dissection with the electrosurgical unit on the large surface area of the abdominal fascia. Work was continued with the laser, however, up to the level of just below the umbilicus. At this point, the incision was along the full length of the suprapubic scar and converted to an open approach, using the electrocautery. The electrocautery was about 5 times faster than using the YAG laser. A more powerful laser would likely to have been more effective.

From this first attempt, it was learned that there would be considerable technical difficulties in obtaining good exposure, hemostasis, smoke evacuation, fluid evacuation, keeping the tip of the scope clean to provide a continuous image, keeping the electrode tip or laser tip in position in view on the monitor to facilitate working with it, and do all six of these things at the same time to enable functioning as a surgeon to perform the technical feat of an endoscopic abdominoplasty while watching the TV monitor.

It was then decided to alter the approach and try to become proficient in each step or each part of the procedure by "practicing" each stage on standard open abdominoplasties. The most difficult part of the endoscopic technique was the dissection. This required the most eye hand coordination. It also required the maximum effort and attention of the surgeon, assistant, scrub nurse, and even a second assistant (if available).

When a patient was available for an open abdominoplasty, the procedure was started by making routine markings, followed by a 5 cm incision in the suprapubic area and beginning the dissection using endoscopic techniques. The endoscopic technique was continued as long as the dissection could be done at about the same speed as the open technique. If technical problems of whatever nature were encountered, so as to get 15 to 30 minutes behind, the procedure was converted to the open technique su as not to cause the procedure to run too long. This method of practice takes a little extra effort and adds a little more time to an open procedure; however, it is the most effective way for the surgeon and his team to become proficient in the endoscopic technique. The surgeon and his team can soon accumulate several hours experience by using this technique of 15 to 30 minutes endoscopic practice on each open abdominoplasty.

The second most difficult part of the endoscopic abdominoplasty is the repair of the fascia. Initially, repair of the fascia was made by suturing through the 5 cm incision. A number of procedures were carried out showing that this could be done. However, suturing is difficult to do and the time consuming. At that point, the procedure of U.S. Pat. No. 5,329,945 was developed using fascial stapling. Initially the staple closure was reinforced with a running suture of 1-0 Mersilene.

After using this procedure on 4 open abdominoplasties as described above, after the dissection, the abdominal incision was closed together with skin staples, leaving a 5 cm opening in the suprapubic area. This "incision" plus an additional incision, usually a circumumbilical incision, were used as endoscopic portals to practice the endoscopic repair of the abdominal fascia with the staples. After the repair was completed, the skin staples could be removed to give a perfect view of the endoscopic fascial repair with the staples. The first four of these patients had the staples reinforced with 1-0 Mersilene. Reinforcement of the staple repair is no longer required on any patient. Sufficient clinical experience has shown that the staple repair of the fascia is even stronger than any repair obtained with sutures.

Criteria for selecting a patient for the endoscopic abdominoplasty are as follows:

(1) Patient preference and motivation are the most important issue. If the patient simply will not accept the scar from an open abdominoplasty and evaluation reveals the need for a muscle-fascia repair, then an endoscopic approach is the only choice.

2. The patient must not need a panniculectomy.

3. The patient must have enough diastasis recti and fascial laxity to benefit from the repair.

4. Should a patient have some loose skin, if in the surgeon's opinion the skin will shrink down with liposuction, the patient could be an endoscopic candidate.

5. Liposuction must be used as an adjunctive therapy in the majority of endoscopic abdominoplasties.

6. Just as a surgeon in any specialty who does endoscopic surgery will always inform the patient of the possible need to convert to an open technique if certain intraoperative complications arise, plastic surgeons must likewise inform our patients of the same possibility. Patients should also be advised that should postoperative complications arise, all complications my not be completed via the endoscopic route. If the patient cannot accept these possibilities, then an endoscopic approach should not be used.

7. Since endoscopic surgery is considered by the general public to be high tech, the expectations of many patients my be unrealistic. Be certain to give informed consent that is designed to engender realistic expectations.

8. Finally, the patient should always be informed as to the surgeon's level of expertise in any new procedure or technique which is to be carried out.

DESCRIPTION OF THE PREFERRED EMBODIMENTS

The Surgical Instruments

Referring to the drawings by numerals of reference, and more particularly to FIGS. 2-7, there are shown several instruments used in the procedure for endoscopic assisted abdominoplasty as described hereinafter. These instruments are all available commercially and have been used in other procedures. A combined tenaculum and stapling gun is contemplated for use in this procedure and is probably novel when developed.

A cervical tenaculum 10 (FIG. 2) comprises a pair of scissors type handles 12 with clamping ends 12 having teeth 13 which will bite into the fascia for plication and stapling in accordance with this procedure.

Figure 3:
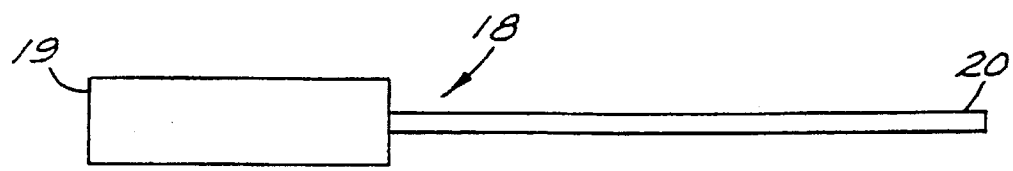
FIG. 3 is a side elevation of an electrosurgical instrument having provision for electrosurgery or electrocauterization used in the surgical procedure of this invention.

An electrosurgical instrument 18 is shown in FIG. 3. Instrument 18 has a handle 21 and cutting and/or cauterizing tip 20 for cutting and cauterizing in this surgical procedure.

Figure 4:
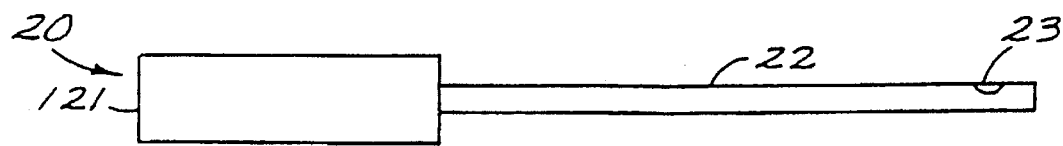
FIG. 4 is a side elevation of a tubular instrument for liposuction used in the procedure of this invention.
Figure 5:
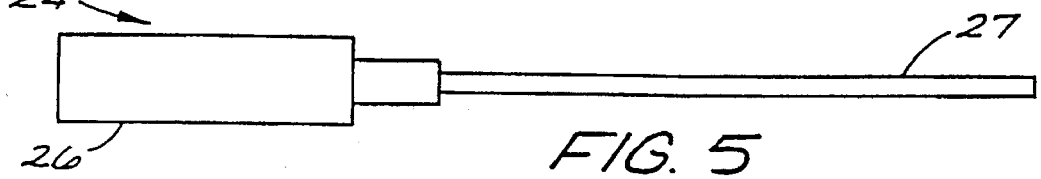
FIG. 5 is a side elevation of an instrument for endoscopic viewing and control of the surgical procedure of this invention.
Figure 6:
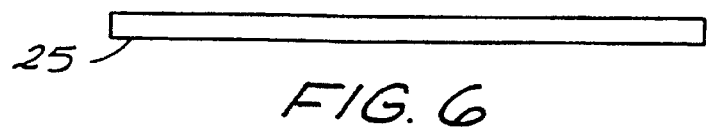
FIG. 6 is a side view of an endoscopic tube for introduction into the body and receiving the endoscopic viewing instrument shown in FIG. 5.

An liposuction instrument 121 is shown in FIG. 4. Instrument 121 has a handle 21 and tubular extension 22 with a side opening 23 for applying suction to remove the fatty layer underlying the skin prior to plication and stapling thereof.

A viewing instrument 14 and endoscopic tube 25 (FIGS. 5 and 6), preferably formed of surgical stainless steel or a hard plastic such as polyurethane or polycarbonate, comprises a handle 26 and endoscopic viewing tube 27 of sufficient length to extend through and out of the end of endotube 25 during use.

There are several good scopes and cameras on the market. The least expensive cameras will be the one chip cameras, which cannot be soaked to sterilize, but instead must be covered with a sterile sleeve. The cameras which will give you the best images are the three chip cameras which can be soaked to sterility. They are also the most expensive cameras. These three chip cameras are like studio quality, and on the high quality monitors available in most operating rooms, they will give an excellent image which greatly enhances your eye-hand coordination, and can give you excellent video tape. Any size scope can be used, but the scope needs to be approximately 30 cm long in order to allow good visualization up to the xiphoid. A 10 mm scope is best because it will allow more light to pass into the operative field and more light, thus a better image, to pass back through the camera and to the monitor.

In surgery the following are used:

| SURGICAL SUPPLIES | INSTRUMENTS |
| --- | --- |
| laparotomy pack | Plasitic set |
| Electrosurgical pencil | Deaver retractor |
| Teflon Bovie blade | Harrington retractor |
| Bovie Blade extender | Liposuction cannulas |
| Asepto syringe | Video camera |
| Suction tubing | 10 mm scope |
| Lap sponges | Cervical tenaculum |
| Antifog | SUTURES |
|  |  |
| Raytecs | *Fascial Staples ×2 |
| 10 & #15 blades | *Skin Staples |
| Marking pen | (3-0 Prolene PS-5 ×1 |
| 3M 1010 Steridrapes ×6 | 3-0 silk PS-2 ×1 |
| Liposuction tubing | 2-0 Vicryl FS-1 ×1 |
| Suction drains ×2 | *used only in embodiment |
| Methylene blue | using staples |
|  | DRESSINGS: |
|  |  |
|  | Cottonball, Benzoin, Steri-Strips |
|  | Abdominal Binder, 4 × 4 sponges |
|  | ABD's ×4; Kerlix ×2 |

Surgical Procedure for Endoscopic Assisted Abdominoplasty

FIG. 1 (collectively) may be referred to as illustrating traditional or standard procedures for abdominoplasty of the abdomen. FIGS. 1A–1I show nine different procedures for abdominoplasty of the abdomen involving incisions through the abdomen. These procedures have been developed in an effort to minimize scarring but have not been able to eliminate visible scars.

In FIGS. 7–18, a surgical procedure is described, utilizing the instruments of FIGS. 2–6 which is a totally new and innovative combination of techniques for abdominoplasty of the abdomen. All procedures (shown in FIGS. 7–18) were performed under general anesthesia.

Once a particular patient has been selected as a candidate for the endoscopic abdominoplasty, preoperative photos and video are made. The patient is allowed to have the surgery as an outpatient unless multiple procedures are scheduled or other medical problems dictate the patient be an inpatient. Routine lab work, EKG and chest X-ray if indicated, and an HIV are obtained on every patient.

On the day of surgery the patient is seen preoperatively in the preanesthesia area. In the standing erect position the areas of the abdomen and flanks that need liposuction are marked.

Figure 7:
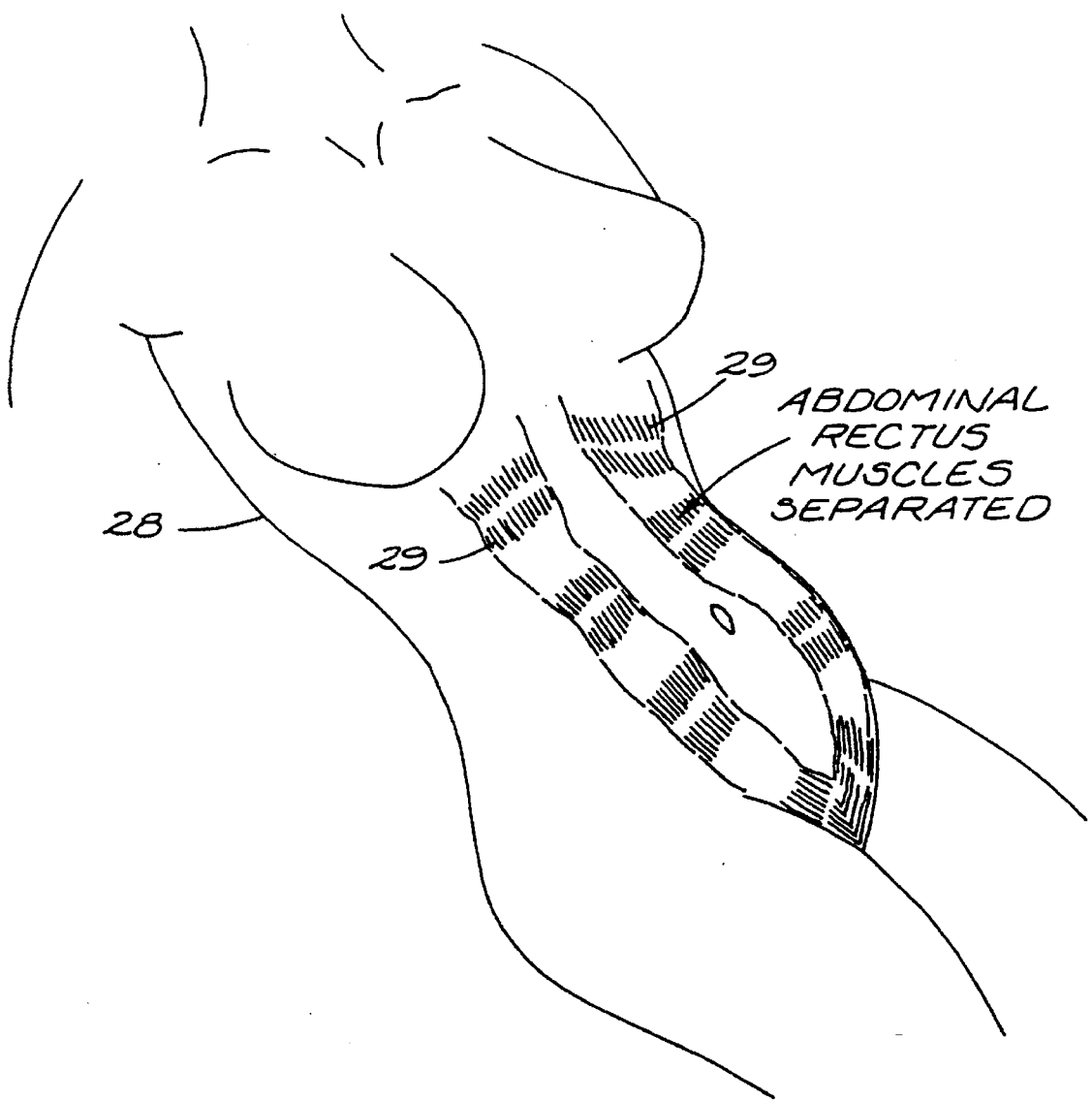
FIG. 7 is a schematic view of a female torso showing a condition with separation of the abdominal rectus muscles requiring the surgical procedure of this invention.
Figure 8:
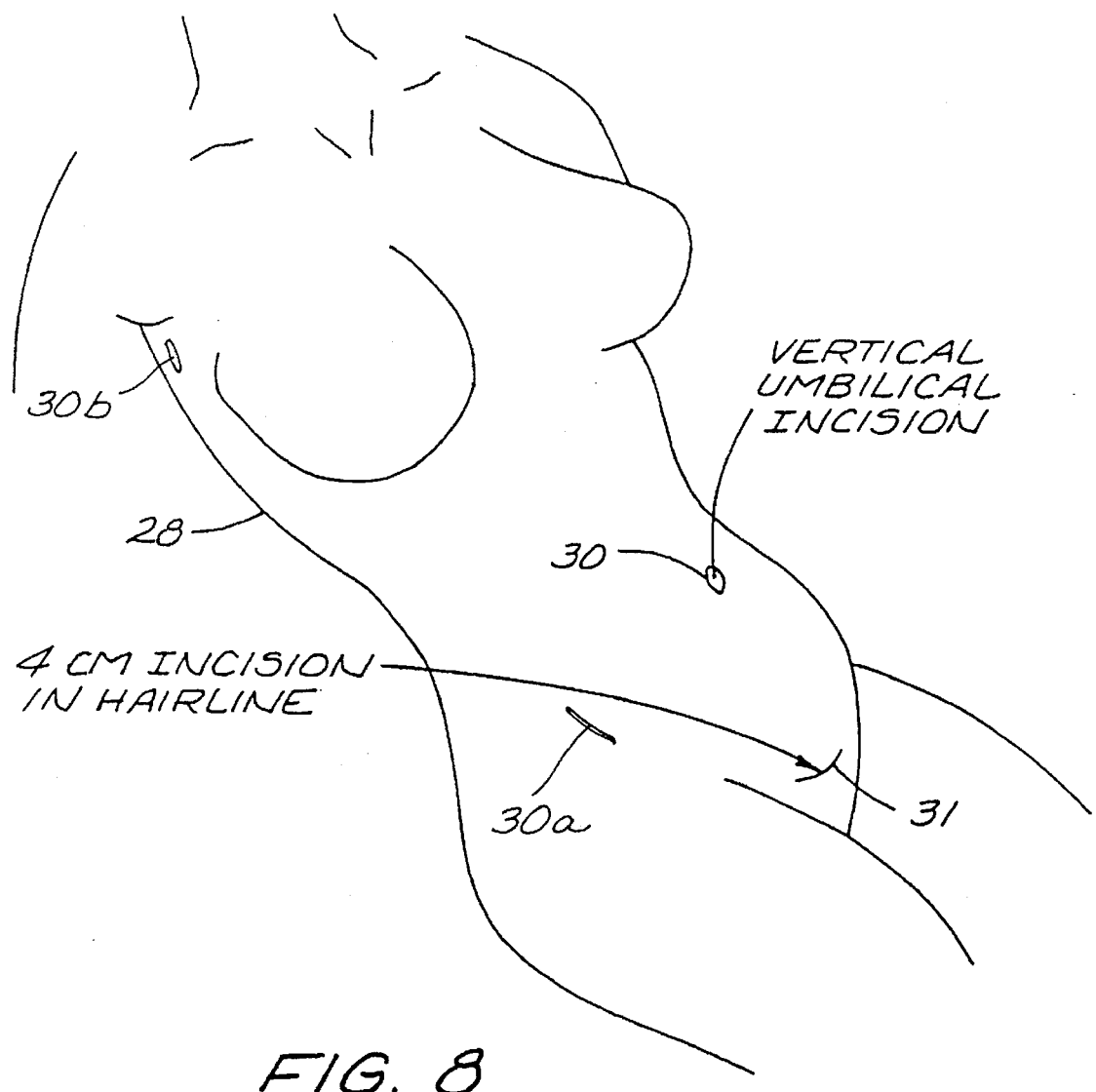
FIG. 8 is a schematic view of a female torso, as in FIG. 7, showing a short vertical umbilical incision and a short incision at the public hair line comprising initial steps in the surgical procedure of this invention.
Figure 9:
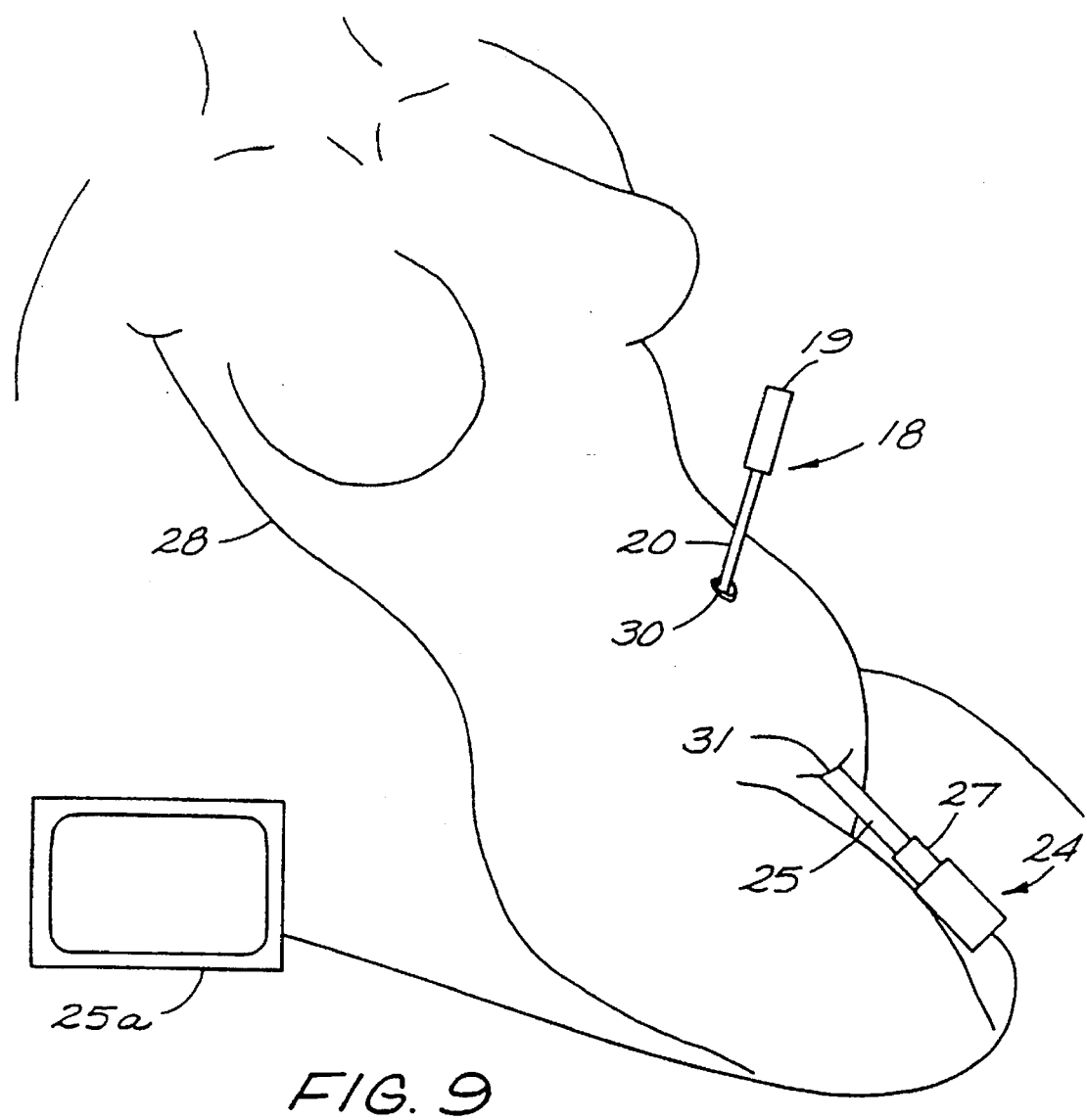
FIG. 9 is a schematic view of a female torso, as in FIG. 8, with the electrosurgical instrument of FIG. 3 inserted through the umbilical incision and the endoscopic tube and viewing instrument inserted through the pubic hair line incision.
Figure 10:
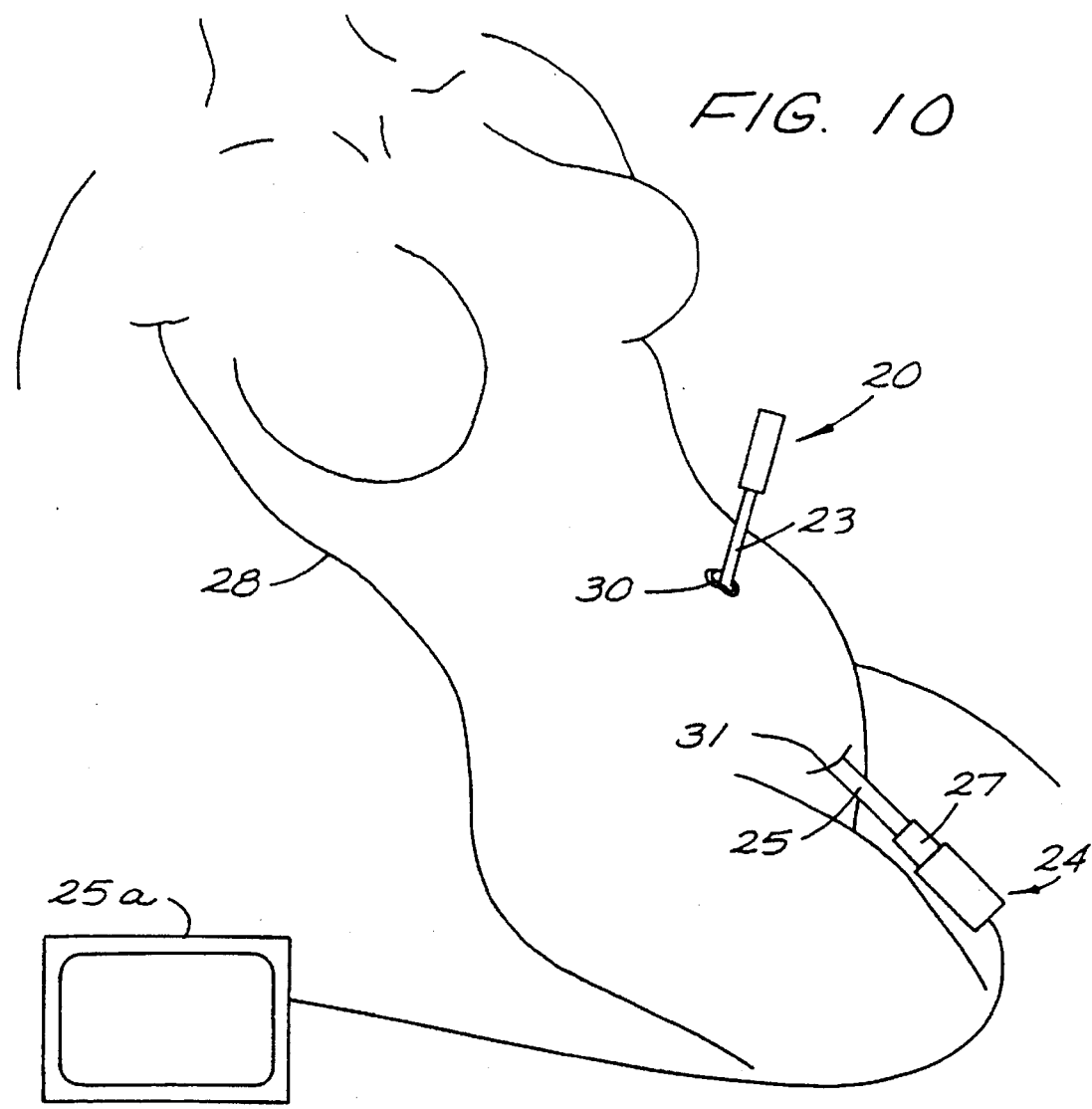
FIG. 10 is a schematic view of a female torso, as in FIG. 9, with the electrosurgical instrument of FIG. 3 removed and the liposuction instrument of FIG. 4 inserted through the umbilical incision and the endoscopic tube and viewing instrument inserted through the pubic hair line incision.
Figure 11:
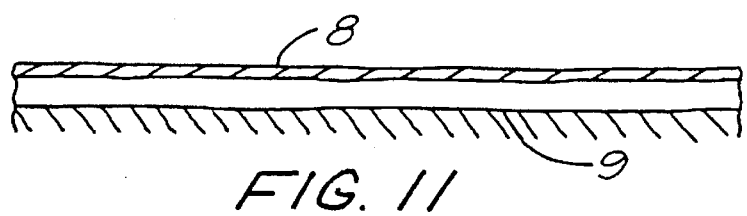
FIG. 11 is a sectional view through the skin, fascia and muscle portion of a body undergoing this surgical procedure and showing the undermining of the skin and separation of the skin layer from the underlying fascia.
Figure 12:
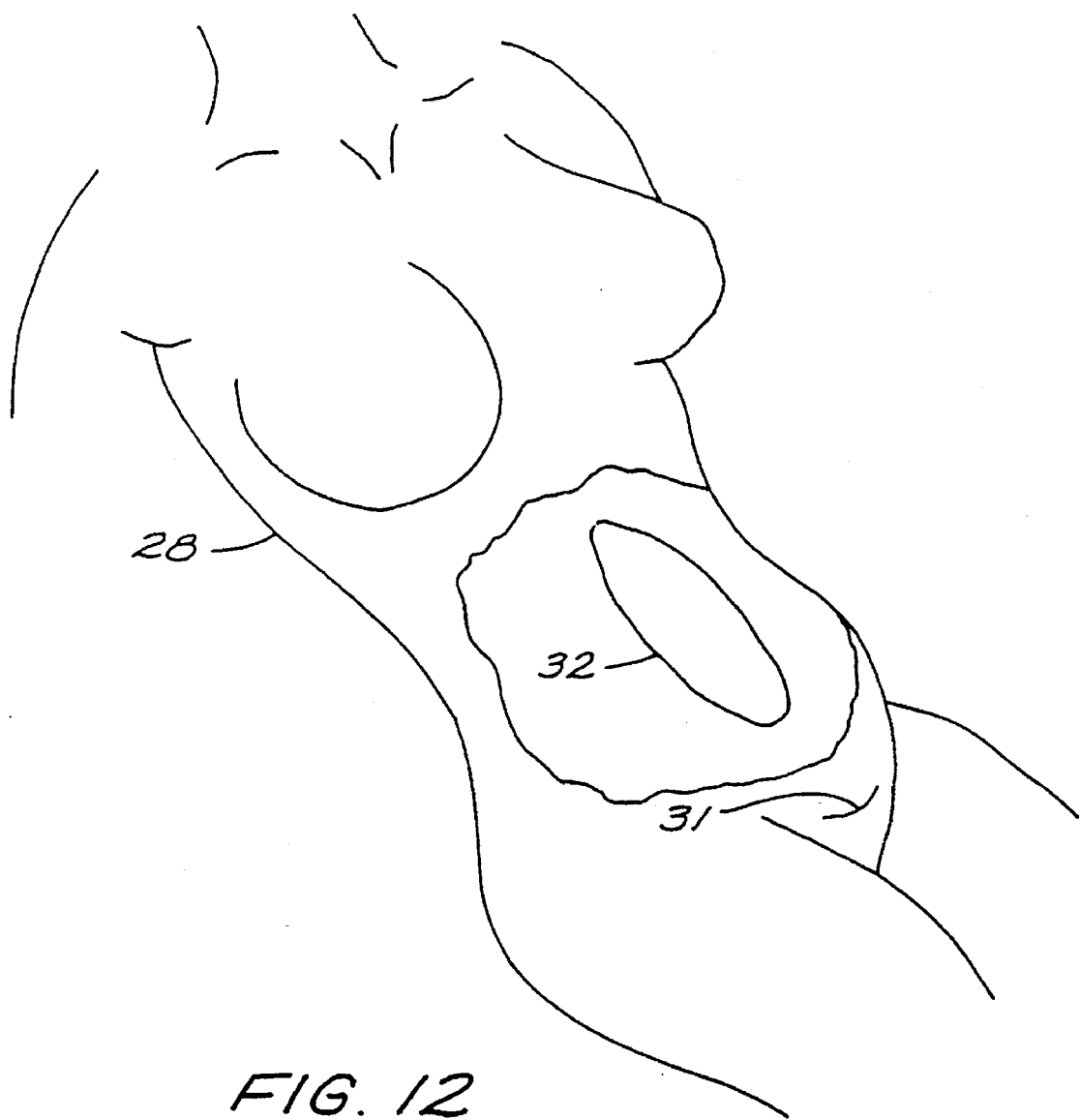
FIG. 12 is a view of a female torso, broken away in front to show the underlying fascia and the marking applied in preparation for plication and suturing.

In FIG. 7, there is shown the torso 28 of a female patient needing an abdominoplasty of the abdomen. This view shows the fascial and muscular area beneath the skin an shows the separation of the abdominal rectus muscles 29 which results in the condition requiring surgical repair.

The patient is taken to the operating room and placed under general endotracheal anesthesia. Hair over the abdomen and mons pubis is shaved. An indwelling Foley catheter is inserted. The abdomen is prepped and draped in the same manner as for the open abdominoplasty. Markings are then made from the suprapubic area out over the iliac crest, up the lateral flanks, across the lower costal margin and Xiphoid, and along the same areas on the opposite side.

All patients are given IV antibiotics preoperatively. The actual surgery begins by making the 5 cm suprapubic incision inside the pubic hair line. The initial dissection can be done under direct vision using the electrocautery. Dissection is carried down to the rectus fascia and following the skin markings made on the abdominal skin, the "pocket" is developed as the skin and subcutaneous tissue are separated from the anterior abdominal fascia. It is very important to get a clean dissection of the fat and soft tissue off the fascia. If a clean dissection is not obtained, when the time comes for the placement of the fascial staples, the integrity of the muscle-fascial repair may be severely compromised.

The patient 28 (FIG. 8), after anesthesia, is given a 5 cm long mark for the suprapubic incision 31 and a 1 cm mark immediately to the left of the 5 cm mark for an incision to insert the endoscope. An incision 30 is made in the umbilicus from the 12 o'clock position to the 6 o'clock position. The incision may be extended along the umbilical rim from 12 to 9 o'clock and from 6 to 3 o'clock if that is necessary to give more length to the incision. The umbilical incision will have to be able to stretch to at least 3 cm to allow the eventual insertion of the upper retractor and the electrosurgical pencil for dissection and the staple gun for closure of the fascia and muscle. The 1 cm suprapubic incision is ideally located to place a 10 mm endoport or surgiport through which the 10 mm endoscope can be place to keep it out of our way as we work with a retractor and electrosurgical pencil. The port is very useful to withdraw the endoscope into to prevent getting blood on the tip and blurring the image. Existing scars 30a and other areas, e.g., under the armpit 30b, can be used for incisions in place of one or more of the above described incisions.

Many plastic surgeons have made small or short incisions above the pubic hair line to take out a small piece of skin and do a limited repair of the muscle and fascia, usually below the umbilicus, and using sutures. There have been no reports of plastic surgeons using endoscopic assistance to accomplish the dissection through such a small incision. Endotube 25 is inserted into incision 31 staying just above the fascia of the interior abdominal wall and below the subcutaneous tissue and fat. The endoscopic tube 27 is introduced to verify position of the surgical instruments and to inspect for bleeding.

Electrosurgical instrument 18 has its cauterizing and cutting tip 20 introduced through umbilical incision 30 and manipulated to undermine the skin for a considerable distance around the incision 30. The cutting and cauterizing by instrument 18 is observed on monitor 25a through endoscopic viewing tube 27. Views of the actual procedure are shown in FIGS. 14–17, below.

Once the first few centimeters of the pocket are opened, the tip of the endoscope is placed inside the pocket and the dissection continued using a combination of direct vision and endoscopic vision via the monitor. As the dissection is carried out in the area below the umbilicus the surgeon needs two assistants. The right handed surgeon standing on the patient's right side needs a scrub nurse or one assistant on the patient's left side, standing at or slightly below the level of the pubis. This assistant should be the one who holds and positions the scope and camera. As the dissection proceeds in a semicircle out from the incision and the pocket depth exceeds 6 to 8 cm, we make the 1 cm incision approximately 1 cm to the left of the 4 cm suprapubic incision, insert the 10 mm port and introduce the endoscope through the port. This allows the assistant to maintain much better control of the scope and camera.

As long as the dissection remains below the umbilicus the surgeon can maintain most of the retraction with the left hand and the manipulation of the electrosurgical pencil with the right hand. The second assistant will be on the left side of the patient and will assist the surgeon hold the retractor. The two retractors we use (Harrington and Deaver) have both been modified with a metal suction tube that can be attached to wall suction and functions to keep the electrocautery smoke and vapors evacuated from the surgical area. Smoke evacuation is vital to maintain satisfactory visibility.

As the dissection approaches the umbilicus, the previously described vertical incision 30 is made in the umbilicus. This divides the umbilicus into two halves, right and left. Each half is detached from the rectus fascia-umbilical stalk. This is done under direct vision. The dissection is continued underneath the divided and elevated umbilicus. Once we have completed the dissection to a level of the umbilicus, we replace the Deaver retractor in the suprapubic incision with the Harrington retractor, we keep the endoscope coming through the port beside the suprapubic incision, and we relocate the Deaver retractor to the umbilical incision. The suction tubing can be attached to either retractor. We generally have it attached to the retractor closest to area we are working with the electrocautery.

At this point the surgeon must have two assistants. One must devote his full attention to the placement and control of the endoscope. The other must maintain retraction on the Harrington retractor in the suprapubic incision to keep the pocket open for visibility and preventing contact of the flap and bloody tissue with the scope tip. It is possible for the surgeon using an extension tip for the electrocautery to continue to work the dissection through the suprapubic incision. We find it much easier and a less stressful position to work with the electrosurgical pencil through the umbilical incision. Changing from the suprapubic incision to the umbilical incision, while leaving the scope in the lower incision, will cause the surgeon some minor adaptation of his eye-hand coordination, but the surgeon who has been able to accomplish the dissection from the pubis to the umbilicus will not have any great difficulty making the adaptation.

After completely undermining the area of skin below which the procedure is to be carried out, electrosurgical instrument 18 is withdrawn and liposuction instrument 20 has its tip 23 inserted through umbilical incision 30 and the fat aspirated out through opening 23 by vacuum (not shown). In most cases, liposuction is a necessary step in the procedure since the removal of fat is required for efficient plication of the underlying fascia and muscle. However, if a patient is especially lean and has little or no subcutaneous fat, but requires the abdominoplasty because of muscular separation, the liposuction may be omitted. In traditional abdominoplasties, liposuction is not used because of the bleeding caused by the large incision through the abdomen.

Many plastic surgeons have used liposuction as an adjunct to an abdominoplasty, however in a fully undermined abdominoplasty (as done with this Endoscopic Technique) when done through the standard long incision, full and complete liposuction of the abdomen is usually not done due to the loss of blood supply from arteries and veins severed by the long incision. However with this Endoscopic Technique these arteries and veins are not cut, so there is no problem in doing a complete liposuction of the abdomen.

After completion of the surgical separation of the skin layer from the underlying fascia and muscle (FIG. 9) and liposuction (FIG. 10) of the fat layer, the patient is ready for the plication and repair of the fascia and separated rectus muscle. The fascia is exposed up to the xiphoid, then laterally out over the rib cage far enough to be certain the skin flap has room to spread out smoothly rather than bunch up in the epigastric area when we begin the fascial plication. At this point, exposure of the fascia is completed over the entire anterior wall in the area planned and marked just prior to incision. Once the fascia has been plicated, further dissection may be needed, especially in both lateral areas, to allow for better redraping of the skin.

If the fascia or the pocket is bloody, irrigation and drying of the surface of the fascia is done as much as possible with sponges. In an open abdominoplasty, the exposed fascia dries out if not kept moistened. However, with the endoscopic approach the fascia is not exposed and does not dry out during the procedure. An estimate is made as to how tightly the fascia would be plicated if an open abdominoplasty were being done and using a Q-tip and methylene blue an ellipse is marked on the fascial surface that approximates the amount can likely be plicated.

Endoscopic or direct viewing via incision 31 allows the surgeon to view and control the procedure of plication and suturing. As a preliminary step, an elliptical marking 32 of methylene blue is inscribed on the fascia below the undermined skin and surrounding the separated rectus muscle area which is to be repaired.

Figure 13:
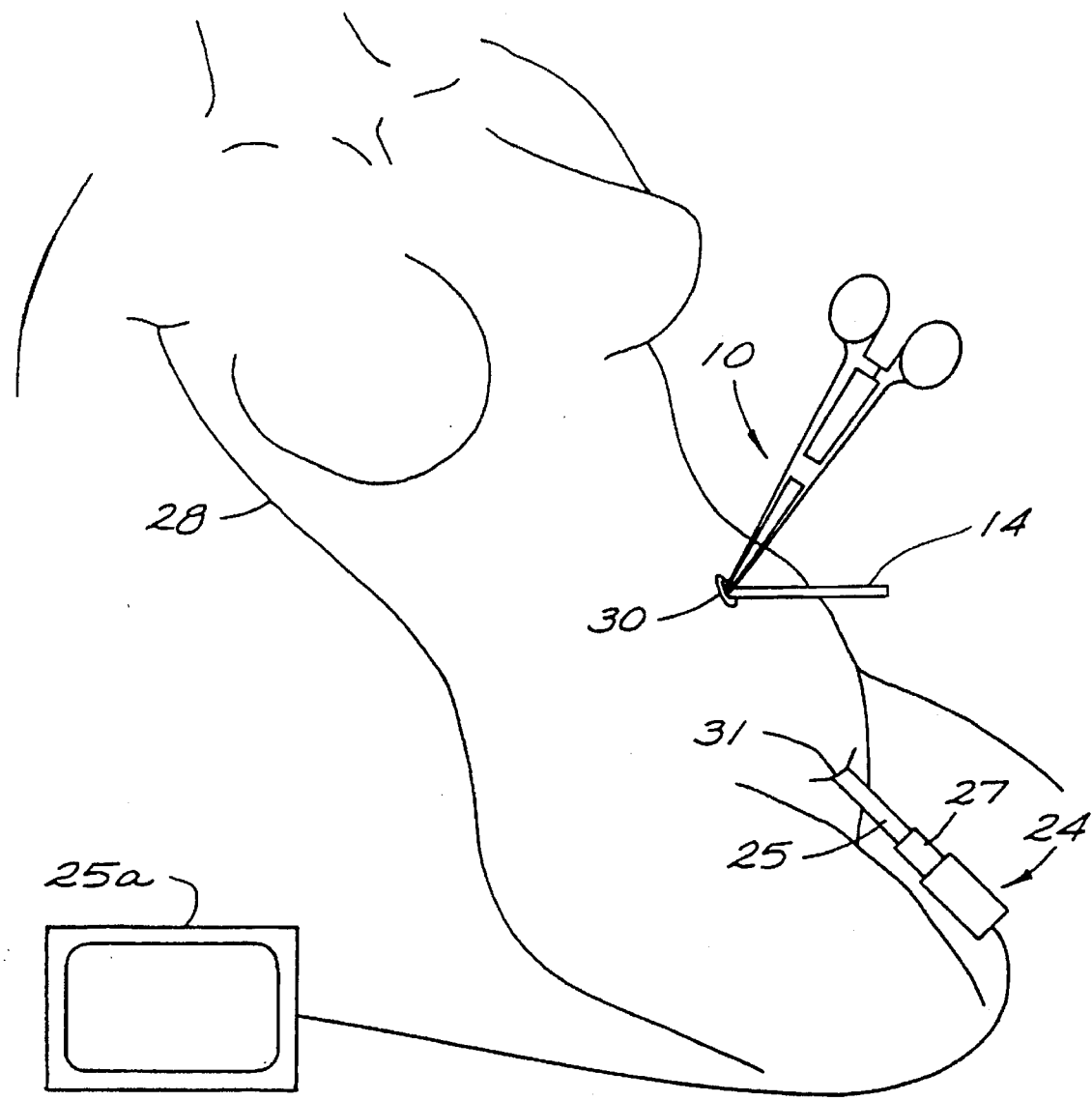
FIG. 13 is a sectional view of a female torso, as in FIG. 7, with the electrosurgical and liposuction instruments removed and the tenaculum of FIG. 2 and a surgical suturing needle inserted through the umbilical incision.
Figure 14:
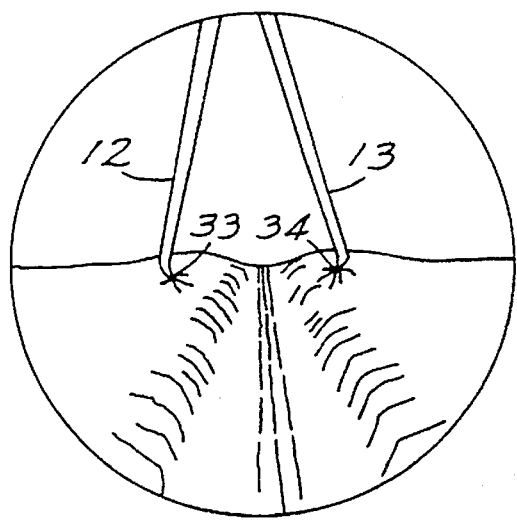
FIG. 14 is a view as seen through the endoscopic viewing instrument of the surgical procedure showing the application of the cervical tenaculum grasping the fascia in preparation for plication and suturing.
Figure 15:
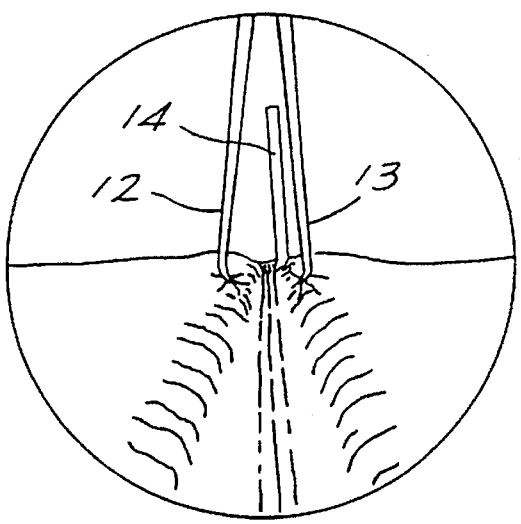
FIG. 15 is a view as seen through the endoscopic viewing instrument of the surgical procedure showing the cervical tenaculum clamping the fascia to plicate it and the suturing needle to suture the clamped and plicated portion of the fascia.

The plication and suturing of the fascia and muscle of the abdominal wall is carried out in a sequence of steps shown in FIGS. 13–17. First, as seen in FIG. 13, the cervical tenaculum 10 and tip of the suturing needle 14 are inserted through the umbilical incision 30. The procedure can be seen on monitor 25a during all stages. The pointed tips 12 and 13 of tenaculum 10 grip spaced points 33 and 34 (about 12–24 cm. apart) on elliptical mark 32 (FIG. 12) on the abdominal fascia and muscle (FIG. 13).

Then, the tips 12 and 13 are squeezed together (FIG. 15) to begin the plication of the abdominal fascia. The suturing needle 14 is pressed into the plicated portion of abdominal fascia adjacent to the squeezed-together tips 12 and 13 of tenaculum 10 and surgical suture 17 applied. The surgical suture 17 penetrates the plicated portion of the fascia and draws the plicated fascia together and secures it in place.

Figure 16:
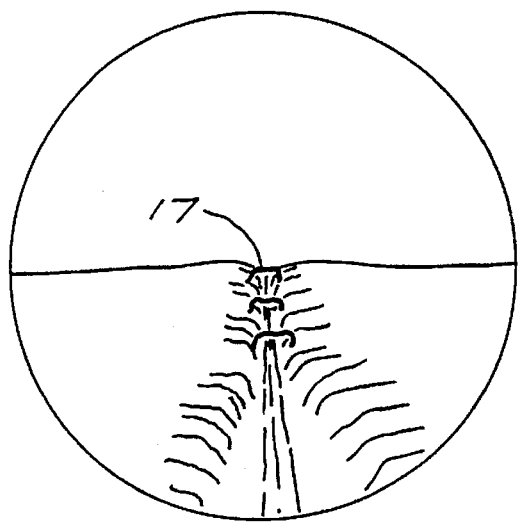
FIG. 16 is a view as seen through the endoscopic viewing instrument of the surgical procedure showing a portion of the clamped and plicated fascia with part of the suturing completed.
Figure 17:
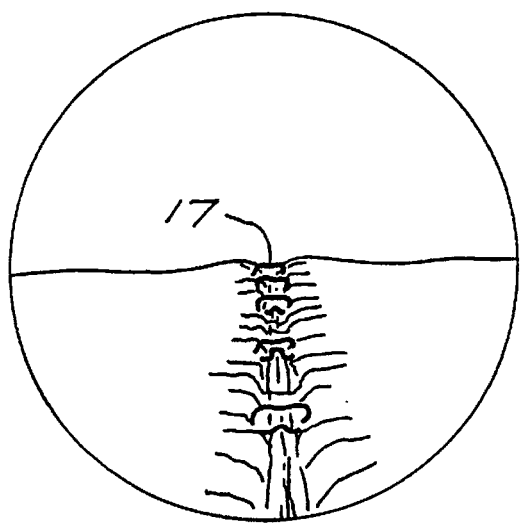
FIG. 17 is a view as seen through the endoscopic viewing instrument of the surgical procedure showing the substantially completed plication and suturing of the fascia in repairing fascial muscle tissue.
Figure 18:
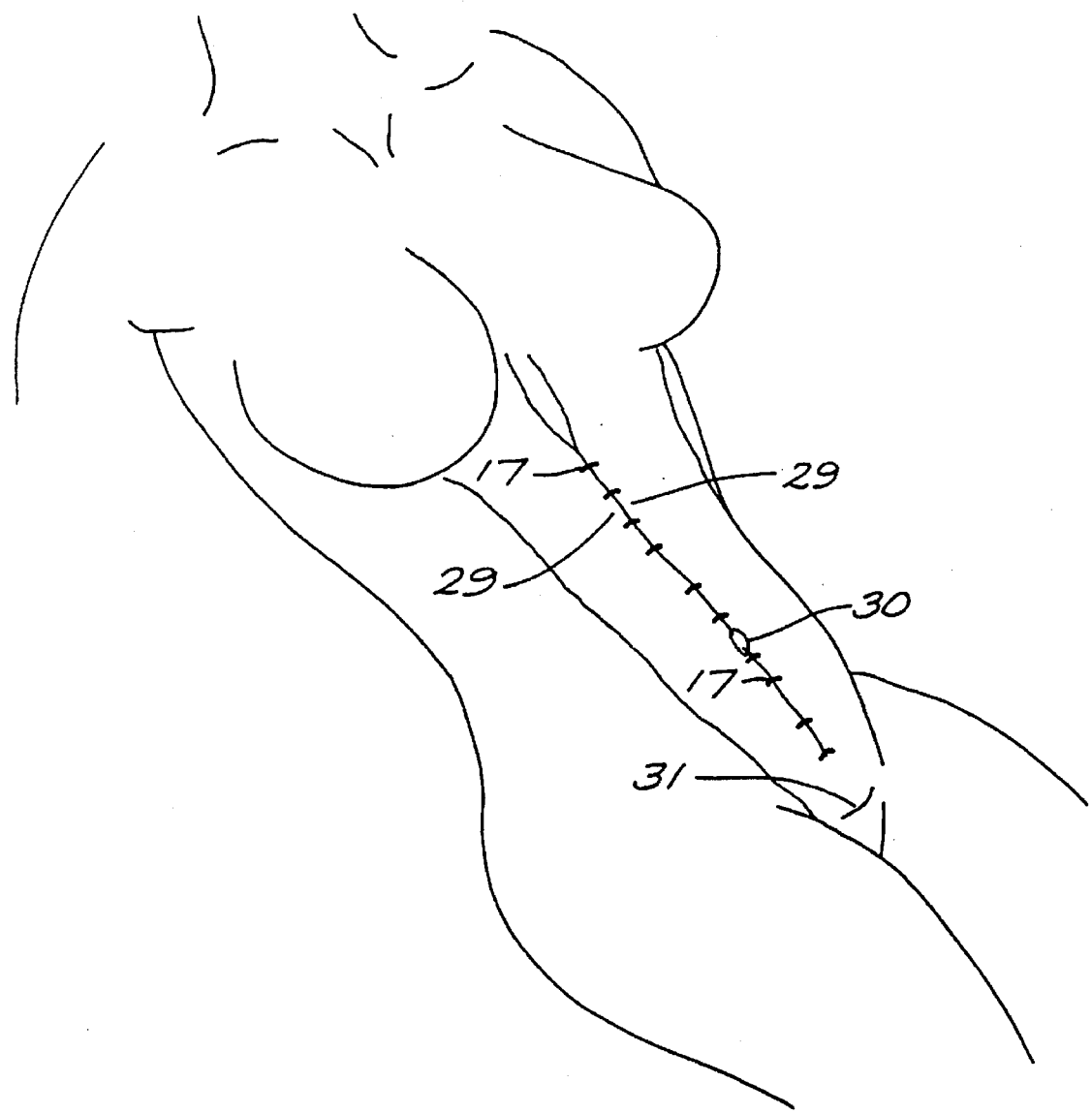
FIG. 18 is a view of a patient below the level of the skin showing the completely placated and sutured fascia produced in accordance with FIGS. 14–17.

This procedure is repeated in a series of interrupted plicating and suturing operations at about 4–6 cm. intervals along the plicated fascia (FIG. 16). This is followed by plicating and suturing the fascia at points intermediate the 6 cm. spacing using interrupted or running sutures to give a closer reinforcing pattern. Then, the tenaculum 10 is removed and additional sutures applied, if necessary, to fill in the spacing of the sutures 17 (FIG. 17). In FIG. 18, a view of the fascial and muscular area beneath the skin, similar to FIG. 7, shows the repair of the abdominal rectus muscles 29 by the plication and suturing just described. If the area of undermining of the skin appears to be insufficient at the conclusion of the plication and suturing procedure, additional undermining may be performed with the cutting and cauterizing instrument 18 as a final procedure.

Closure of the umbilical incision is accomplished by suturing the right half of the umbilicus to the fascia with a suture of 2-0 Vicryl. The two halves of the umbilicus are then sutured together with a running suture of 3-0 Prolene. Two Jackson-Pratt drains, 10 mm, full length perforated are placed one in each lateral sulcus and brought out through the suprapubic incision. That incision is closed with subcutaneous sutures of 2-0 Vicryl and skin staples. The drains are sutured in place with 3-0 silk. The 1 cm endoscope incision is closed with one or two skin staples. Dressings of 4×4s, Kerlix, and ABD's are applied and an abdominal binder is put in place.

At the conclusion of the procedure, the umbilical incision 31 and the pubic area incision 30 are then sutured and a cotton ball compress and/or bandage put in place. The patient can go home directly from the recovery room without requiring hospitalization. The natural elasticity of the skin causes the undermined skin to contract or shrink down to conform to the new abdominal wall and adhere to the repaired fascia, thereby not requiring the long incisions needed to remove skin and leaving long ugly scars.

The postoperative care is basically the same as with the standard open abdominoplasty. The patients feel very little need to bend forward when they are erect because there has been no skin excision to result in a long lower abdominal incision closed under tension. All patients were given intraoperative antibiotics and are placed on oral antibiotics post operatively. They were also given a strong oral analgesic for pain control, except inpatients can receive intramuscular or intravenous medications. The drains were left in for 7 days and the patients were instructed how to empty the evacuation containers. Another extremely important thing the patient must be instructed to do is to loosen and reposition the binder no less than four times a day. A compressive bandage that folds, rolls, or ridges in a given place on the abdomen, if left there too long can produce a permanent deformity just as garments or bandages applied after liposuction can do.

Experience over the past 20 years doing the standard open abdominoplasties has shown an incidence of seroma formation that is at least equal to that reported in the literature. The incidence of seroma formation in the limited incision or "mini" abdominoplasties, especially with associated liposuction of the abdominal pedicle, is frequently higher. Therefore, it was not surprising when endoscopic abdominoplasty revealed prevention or treatment of seroma formation was needed. The patient is advised to reposition the binder frequently to help prevent swelling of the abdominal flap, and hold it evenly in place so it can reattach to the fascia. The patient is advised to wear the binder for 3 weeks and then wear a good fitting panty girdle for another 6 weeks, or until all the swelling has subsided.

The results of this new and improved endoscopic assisted abdominoplasty were evaluated on the basis of several procedures performed during May–December 1992.

From the foregoing description, it is seen that, the Endoscopic Assisted Abdominoplasty technique combines several surgical techniques into a completely new procedure to avoid extensive scars on the abdomen:

(1) small incisions hidden under the armpit, or in preexisting scars, or on the abdomen or hidden in the umbilicus and inside the pubic hair line.

(2) full and complete undermining of the abdominal skin and fat (as done in the most extensive traditional or standard abdominoplasty) made possible by use of the endoscopic procedure.

(3) complete and effective plication or repair of the muscles and abdominal fascia, from the xyphoid process to the pubis is made possible by use of the endoscope and fascial sutures.

(4) full and complete liposuction of the abdomen can be done which is contraindicated in the traditional or standard abdominoplasty.

(5) this procedure relies on and allows the natural elasticity of the skin to cause the undermined skin to contract or shrink down to conform to the new abdominal wall, thereby not requiring the long incisions needed to remove skin and leaving long ugly scars.

It should be noted, however, that this Endoscopic Assisted Abdominoplasty is not a procedure for all patients. It is basically for the person (frequently women who have had one or more babies) who has weakness in the anterior abdominal muscles (primarily separation of the rectus muscles) and distension of the abdominal fascia. This person may also have additional protrusions of the abdomen due to excessive abdominal fat. However, the person must not have excessive or overhanging abdominal skin where a longer incision is mandatory to remove the excessive skin.

While this invention has been described fully and completely, it should be understood that, within the scope of the appended claims, the invention may be practiced otherwise than as specifically described.

I claim:

1. A surgical abdominoplasty procedure eschewing the use of large abdominal incisions comprising the steps of making at least one small hidden incision, under the armpit, or in a pre-existing scar, or on the abdomen or in the umbilicus of inside the pubic hair line, inserting a surgical cutting and cauterizing instrument through said incision and undermining the skin over a sufficient area of the fascia and muscle to be repaired to permit smooth contraction of the skin over the repaired fascia and muscle, inserting a surgical clamping instrument through said incision, underneath the skin and above the fascia, to engage the fascia at predetermined spaced points and operating the clamping instrument to plicate the fascia, inserting a suturing needle and suture through the incision and suturing the plicated fascia, repeating the procedure at a predetermined spacing along the fascia being repaired to complete the fascial and muscular repair, and suturing or closing said small incision.

2. A surgical abdominoplasty procedure according to claim 1 in which the procedure is carried out to effect complete and effective plication and repair of the muscles and abdominal fascia in the region from the xyphoid process to the pubis.

3. A surgical abdominoplasty procedure according to claim 1 in which selected portions of the surface of the fascia beneath the undermined skin are marked to define the portions of the fascia to be plicated and sutured in the procedure.

4. A surgical abdominoplasty procedure according to claim 1 in which the surface of the fascia beneath the undermined skin is given an elliptical mark to define the portions of the fascia to be plicated and sutured in the procedure, and the plication and suturing drawing together and suturing the fascia along said elliptical mark.

5. A surgical abdominoplasty procedure according to claim 1 in which a second incision is made within the pubic hair line and an endoscopic tube and endoscopic viewing instrument inserted therein to permit observation of the surgical site during the surgical undermining and plicating and fascial suturing procedures.

6. A surgical abdominoplasty procedure according to claim 1 in which fat is removed by liposuction during or after undermining of the skin and prior to plication and fascial suturing.

7. A surgical abdominoplasty procedure according to claim 1 in which a further or supplemental undermining of the skin is carried out, as needed, during or after the plication and fascial suturing steps to assure that the skin is undermined a predetermined distance around the fascial and muscular repair and permit subsequent uniform contraction of the skin over the repair.

8. A surgical abdominoplasty procedure according to claim 1 in which said surgical cutting and cauterizing instrument is an electrosurgical cutting and cauterizing instrument or a laser instrument operable to be inserted through said incision and undermining the skin over a sufficient area of the fascia and muscle to be repaired to permit smooth contraction of the skin over the repaired fascia and muscle.

9. A surgical abdominoplasty procedure according to claim 1 in which said surgical clamping instrument is a cervical tenaculum inserted through said incision, underneath the skin and above the fascia, to engage the fascia at predetermined spaced points and operated to plicate the fascia.

10. A surgical abdominoplasty procedure according to claim 1 in which said surgical clamping instrument is a cervical tenaculum inserted through said incision, underneath the skin and above the fascia, to engage the fascia at distances of about 12–24 cm. and operated to plicate the fascia.

11. A surgical abdominoplasty procedure according to claim 1 in which the procedure is carried out to effect complete and effective plication and repair of the muscles and abdominal fascia in the region from the xyphoid process to the pubis, and selected portions of the surface of the fascia beneath the undermined skin are marked to define the portions of the fascia to be plicated and sutured in the procedure.

12. A surgical abdominoplasty procedure according to claim 1 in which the procedure is carried out to effect complete and effective plication and repair of the muscles and abdominal fascia in the region from the xyphoid process to the pubis, the surface of the fascia beneath the undermined skin is given an elliptical mark to define the portions of the fascia to be plicated and sutured in the procedure, and the plication and fascial suturing drawing together and suturing the fascia along said elliptical mark.

13. A surgical abdominoplasty procedure according to claim 1 in which the procedure is carried out to effect complete and effective plication and repair of the muscles and abdominal fascia in the region from the xyphoid process to the pubis, the surface of the fascia beneath the undermined skin is given an elliptical mark to define the portions of the fascia to be plicated and sutured in the procedure, the plication and fascial suturing drawing together and suturing the fascia along said elliptical mark, a second incision is made within the pubic hair line and an endoscopic tube and endoscopic viewing instrument inserted therein to permit observation of the surgical site during the surgical undermining and plicating and fascial suturing procedures, and excessive fat is removed by liposuction.

14. A surgical abdominoplasty procedure according to claim 1 in which the procedure is carried out to effect complete and effective plication and repair of the muscles and abdominal fascia in the region from the xyphoid process to the pubis, the surface of the fascia beneath the undermined skin is given an elliptical mark to define the portions of the fascia to be plicated and sutured in the procedure, the plication and fascial suturing drawing together and fascial suturing the fascia along said elliptical mark, a second incision is made within the pubic hair line and an endoscopic tube and endoscopic viewing instrument inserted therein to permit observation of the surgical site during the surgical undermining and plicating and fascial suturing procedures, and a further or supplemental undermining of the skin is carried out, as needed, during or after the plication and fascial suturing steps to assure that the skin is undermined a predetermined distance around the fascial and muscular repair and permit subsequent uniform contraction of the skin over the repair.

15. A surgical abdominoplasty procedure according to claim 1 in which the procedure is carried out to effect complete and effective plication and repair of the muscles and abdominal fascia in the region from the xyphoid process to the pubis, the surface of the fascia beneath the undermined skin is given an elliptical mark to define the portions of the fascia to be plicated and sutured in the procedure, the plication and fascial suturing drawing together and suturing the fascia along said elliptical mark, a second incision is made within the pubic hair line and an endoscopic tube and endoscopic viewing instrument inserted therein to permit observation of the surgical site during the surgical undermining and plicating and fascial suturing procedures, and a further or supplemental undermining of the skin is carried out, as needed, during or after the plication and fascial suturing steps to assure that the skin is undermined a predetermined distance around the fascial and muscular repair and permit subsequent uniform contraction of the skin over the repair, and fat is removed by liposuction during or after undermining of the skin and prior to plication and fascial suturing.

16. A surgical abdominoplasty procedure according to claim 1 in which the procedure is carried out to effect complete and effective plication and repair of the muscles and abdominal fascia in the region from the xyphoid process to the pubis, the surface of the fascia beneath the undermined skin is given an elliptical mark to define the portions of the fascia to be plicated and sutured in the procedure, the plication and fascial suturing drawing together and fascial suturing the fascia along said elliptical mark, said surgical cutting and cauterizing instrument is an electrosurgical cutting and cauterizing instrument or a laser instrument operable to be inserted through said incision and undermining the skin over a sufficient area of the fascia and muscle to be repaired to permit smooth contraction of the skin over the repaired fascia and muscle, a second incision is made within the pubic hair line and an endoscopic tube and endoscopic viewing instrument inserted therein to permit observation of the surgical site during the surgical undermining and plicating and fascial suturing procedures, and a further or supplemental undermining of the skin is carried out, as needed, during or after the plication and fascial suturing steps to assure that the skin is undermined a predetermined distance around the fascial and muscular repair and permit subsequent uniform contraction of the skin over the repair, and excessive fat is removed by liposuction.

17. A surgical abdominoplasty procedure according to claim 1 in which the procedure is carried out to effect complete and effective plication and repair of the muscles and abdominal fascia in the region from the xyphoid process to the pubis, the surface of the fascia beneath the undermined skin is given an elliptical mark to define the portions of the fascia to be plicated and sutured in the procedure, the plication and fascial suturing drawing together and fascial suturing the fascia along said elliptical mark, said surgical cutting and cauterizing instrument is an electrosurgical cutting and cauterizing instrument or a laser instrument operable to be inserted through said incision and undermining the skin over a sufficient area of the fascia and muscle to be repaired to permit smooth contraction of the skin over the repaired fascia and muscle, said surgical clamping instrument is a cervical tenaculum inserted through said incision, underneath the skin and above the fascia, to engage the fascia at predetermined spaced points and operated to plicate the fascia, a second incision is made within the pubic hair line and an endoscopic tube and endoscopic viewing instrument inserted therein to permit observation of the surgical site during the surgical undermining and plicating and fascial suturing procedures, and a further or supplemental undermining of the skin is carried out, as needed, during or after the plication and fascial suturing steps to assure that the skin is undermined a predetermined distance around the fascial and muscular repair and permit subsequent uniform contraction of the skin over the repair, and fat is removed by liposuction during or after undermining of the skin and prior to plication and fascial suturing.

\* \* \* \* \*